United States Patent
Chapman et al.

(10) Patent No.: US 6,862,945 B2
(45) Date of Patent: Mar. 8, 2005

(54) CAMERA GUIDE FOR VIDEO PIPE INSPECTION SYSTEM

(75) Inventors: Eric Chapman, Duvall, WA (US); Michael E. Turgeon, San Diego, CA (US); Mark S. Olsson, La Jolla, CA (US)

(73) Assignee: Deepsea Power & Light, San Diego, CA (US)

( * ) Notice: Subject to any disclaimer, the term of this patent is extended or adjusted under 35 U.S.C. 154(b) by 39 days.

(21) Appl. No.: 10/278,549

(22) Filed: Oct. 22, 2002

(65) Prior Publication Data

US 2004/0083829 A1 May 6, 2004

(51) Int. Cl.$^7$ ............................................. G01M 19/00
(52) U.S. Cl. ..................................... 73/865.8; 73/866.5
(58) Field of Search ............................ 73/865.8, 866.5; 348/84, 85; 356/241.6, 241.4

(56) References Cited

U.S. PATENT DOCUMENTS 5,090,259 A * 2/1992 Shishido et al. ............ 73/866.5
5,457,288 A * 10/1995 Olsson .................... 174/117 R

OTHER PUBLICATIONS

Mytana, WNG–4 Camera Wings (one page) www.mytana.com, Jan. 15, 2004.
Pearpoint, P455 Twinview Camera (one page), www.pearpoint.com, Jan. 15, 2004.
Rothenberger, ROCAM® Color (one page), www.rothenberger.de, Jan. 15, 2004.
Vision Technology, 6–8 inch Skid System (one page), www.vtdesign.com, Jan. 15, 2004.
Radiodetection, Skids (one page), www.radiotection.com, Jan. 15, 2004.
Ridgid Kollman, Standard and Mini SeeSnake Diagnostic Equipment manual, p. 16.
Ridgid Kollman, Standard and Mini SeeSnake Diagnostic Equipment manual, p. 17.
Sreco Flexible, Flexi–Cam Camera Brushes and Drag Skids, one page, www.srecoflexible.com, Jan. 15, 2004.
General Pipe Cleaners, Skids (one page), www.generalpipecleaner.com, Jan. 15, 2004.
TV Inspection, Skids (one page), www.trinspection.com, Jan. 15, 2004.

* cited by examiner

*Primary Examiner*—Robert Raevis
(74) *Attorney, Agent, or Firm*—Michael H. Jester

(57) ABSTRACT

A guide for a video pipe inspection system that includes a camera head and a tubular coil spring having a central axis. A guide member with radially extending fins is configured to surround the tubular spring. At least one pin is removably engageable with the guide member and the tubular coil spring to retain the guide member in position with respect to the tubular coil spring. The straight segments of a pair of opposing U-shaped pins can be inserted into grooves in the guide member so that they extend between adjacent coils of the tubular coil spring. In alternate form, the guide member may include an inner capture ring assembly that receives the pins. An outer yoke assembly surrounds, and is freely rotatable about, the inner capture ring assembly and includes a pair of axles for rotatably supporting a pair of wheels that engage an interior wall of the pipe.

20 Claims, 5 Drawing Sheets

CAMERA GUIDE FOR VIDEO PIPE INSPECTION SYSTEM

FIELD OF THE INVENTION

The present invention relates to electromechanical systems for inspecting the insides of pipes and other conduits for defects and obstructions, and more particularly, to mechanisms for connecting guides to coil springs associated with video camera heads used for this purpose.

BACKGROUND OF THE INVENTION

There are many situations where it is desirable to internally inspect long lengths of pipe which are already in place, either underground, in a building, or underwater. For example, sewer and drain pipes frequently need to be internally inspected to diagnose existing problems or determine if there are any breaks causing leakage or obstructions impairing the free flow of waste. It is also important to internally inspect steam pipes, heat exchanger pipes, water pipes, gas pipes, electrical conduits and fiber optic conduits for similar reasons. Frequently, pipes which are to be internally inspected have an internal diameter of six inches or less. It is sometimes necessary to inspect several hundred feet of pipe.

Over the years, video pipe inspection systems have been developed which typically include a camera which is forced down the pipe so that its interior can be viewed on a video display. It is common to record the inspection on a video recorder (VCR). Conventional video pipe inspection systems include a video push cable which provides an electromechanical connection between a rugged camera head enclosing and protecting the video camera and a rotatable push reel which is used to pay out cable and force the camera head down the pipe. The video push cable must be specially constructed in order to be flexible enough to make tight turns yet rigid enough to be pushed hundreds of feet down small diameter pipe. The video push cable must also incorporate electrically conductive cable having the proper impedance for conveying the NTSC or other video signals to the video display unit and additional power and ground conductors. Examples of video push cables are disclosed in U.S. Pat. No. 5,457,288 granted Oct. 10, 1995 to Mark S. Olsson and U.S. Pat. No. 5,808,239 granted Sep. 15, 1998 to Mark S. Olsson. Typically the camera head has a plurality of LEDs that illuminate the interior of the pipe or conduit so that the video camera can obtain a clear and well defined image.

The design of the video camera head and the manner in which it is connected to the distal end of the video push cable is critical to the performance and reliability of a video pipe inspection system. These structures must be rugged, yet the camera head must be compact and its manner of connection to the video push cable must be flexible enough to bend through tight turns. It is also desirable to incorporate an electromagnetic radiation transmitter near the video camera head so that its position can be confirmed with a remote above-ground locator instrument.

Prior commercial video pipe inspection systems have utilized a coil spring aft of the rigid video camera head to surround and protect the connection between the video push cable and the video camera head while providing the required flexibility. It has also been common to provide the camera head with radially extending vanes or bristles to center the camera head in the pipe. The mounting of a properly sized and positioned pipe guide on the video camera head ensures that the interior of the pipe is subjected to more even lighting from the LEDs and ensures that the field of view of the camera is centered along the central axis of the pipe. The pipe guide also gets the camera above any water or muck present at the bottom of the pipe to avoid smears on the protective lens of the camera head. Moreover, a pipe guide facilitates insertion and withdrawal of the video camera head, especially around corners in the pipe or conduit, and reduces wear and tear on the camera head, and in particular, scratching on its protective lens.

FIG. 1 is a diagrammatic illustration of a conventional video pipe inspection system 10. The forward or distal end of a video push cable 12 is coupled through an electromechanical termination assembly 14 to a rugged video camera head 16 which contains a compact black and white or color video camera that includes a charge-coupled device (CCD). A tubular stainless steel coil steel spring 18 surrounds the push cable 12 and is mechanically coupled to the rear end of the video camera head and to the termination assembly 14. The coil spring 18 provides the correct amount of flexibility to permit the video camera head 16 to negotiate tight turns when inserted down the interior of the pipe P. Stainless steel aircraft type cables 19 connects the camera head 16 to the termination assembly 14. The cables 19 limit the extension of the spring and facilitates removal of the camera head 16 if it were to get stuck in the pipe. A plurality of deformable fins 20 are spaced circumferentially around the camera head 16 and extend in radial directions. The fins 20 form a pipe guide that centers the camera head in the interior of the pipe. The push cable 12 is wound into a coil about a rotatable support reel 22. The rearward or proximal end of the push cable 12 is electrically connected through a slip ring assembly (not illustrated) to a signal transmission line 24 to the system electronics 26 that may include a video display screen. The camera head 16 can be pushed several hundred feet down the length of the pipe P. A ferrous element 27 is located inside the coil spring 18 and is driven with a suitable active drive signal from the system electronics 26. The active drive signal may have a frequency of, for example, 512 Hz. The resulting electromagnetic signal emitted by the ferrous element 27 can be sensed by the antennas of a conventional line and sonde locator so that the operator knows exactly which segment of the interior of the pipe P is being displayed. This tells the operator where the blockage or pipe defect is located.

It is not always desirable to permanently mount the fins 20 on the camera head 16. For example, this may increase the diameter of the camera head 16 too much to negotiate turns in the pipe P. Also, if the fins 20 are permanently connected, it may be impossible to withdraw the camera head 16 if the fins 20 become jammed in a bend in the pipe. Moreover, it is often beneficial to have two separate pipe guides mounted in longitudinally spaced locations. The camera head 16 has a short longitudinal dimension, and therefore it would be desirable to releasably mount a pipe guide around the tubular coil spring 18.

Split C—shaped steel rings have been used to externally clamp the cylindrical collar of a vaned guide around the coil spring of a video pipe inspection system aft of the camera head. Expanding locking sleeve assemblies have also been used inside the collars of vaned guides to clamp them around the coil spring of a video pipe inspection system aft of the camera head. These approaches are difficult to install and the guides may not break free if the camera head gets jammed in a pipe.

SUMMARY OF THE INVENTION

In accordance with the present invention, a guide is provided for a video pipe inspection system that includes a camera head and a tubular coil spring rearward of the camera head that has a longitudinally extending central axis. A guide member is configured to surround the tubular spring. At least one pin is removably engageable with the guide member and the tubular coil spring to retain the guide member in position with respect to the tubular coil spring.

The guide member may have radially extending fins or bristles for engaging an interior wall of the pipe and centering the camera head within the pipe. In the preferred form of the invention, the straight segments of a pair of opposing U-shaped pins can be inserted into grooves in the guide member so that they extend between adjacent coils of the tubular coil spring along insertion axes that are substantially perpendicular to the longitudinal central axis of the tubular coil spring. In an alternate form of the invention, the guide member may include an inner capture ring assembly that receives the U-shaped pins. An outer yoke assembly surrounds the inner capture ring assembly. The inner capture ring assembly may be locked to the tubular coil spring with the U-shaped pins. The outer yoke assembly includes at least one axle that rotatably supports a wheel that engages an interior wall of the pipe to facilitate travel of the camera head along the length of the pipe.

DESCRIPTION OF THE PREFERRED EMBODIMENTS

As used herein, the term "pipe" refers to any type of hollow conduit or other structure through which a camera head can be pushed, including, but not limited to, water pipes, drain pipes, sewer pipes, steam pipes, heat exchanger pipes, gas pipes, electrical conduits and fiber optic conduits.

Figure 1:
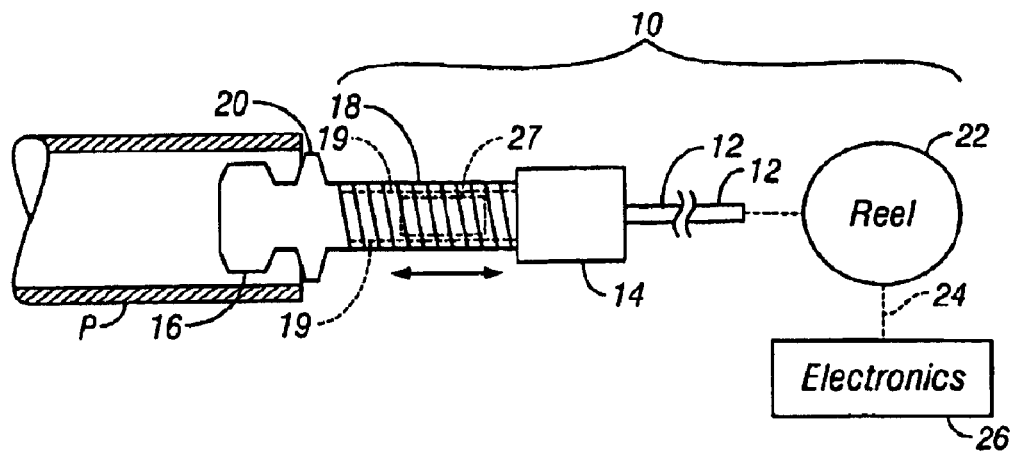
FIG. 1 is a diagrammatic illustration of a conventional prior art video pipe inspection system.
Figure 2:
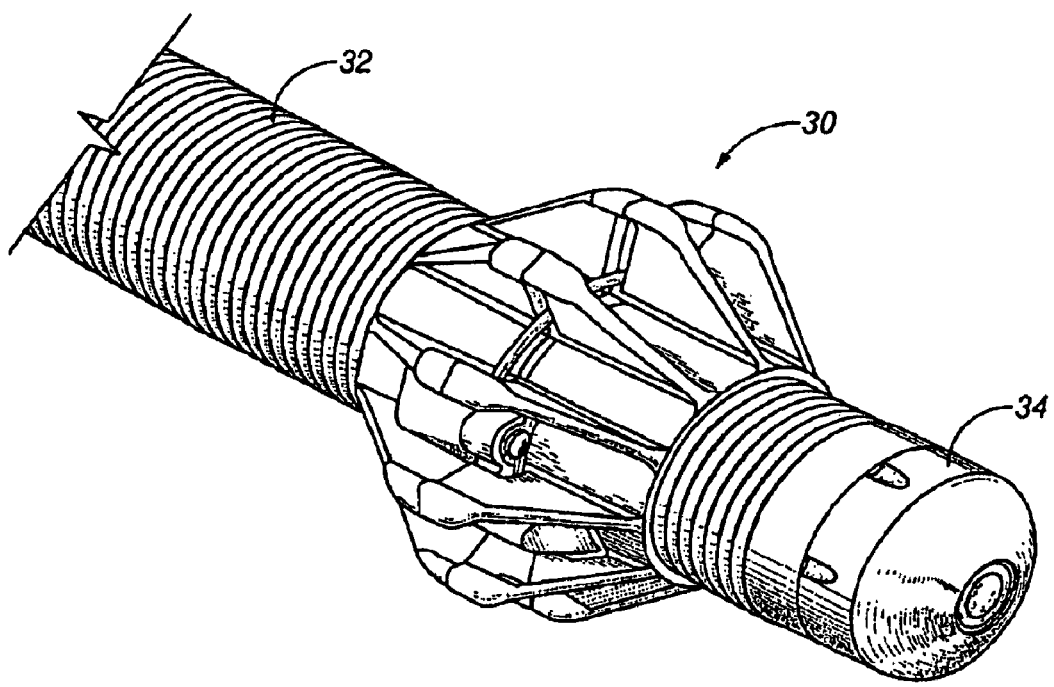
FIG. 2 is a perspective view illustrating a first embodiment of the present invention.
Figure 3:
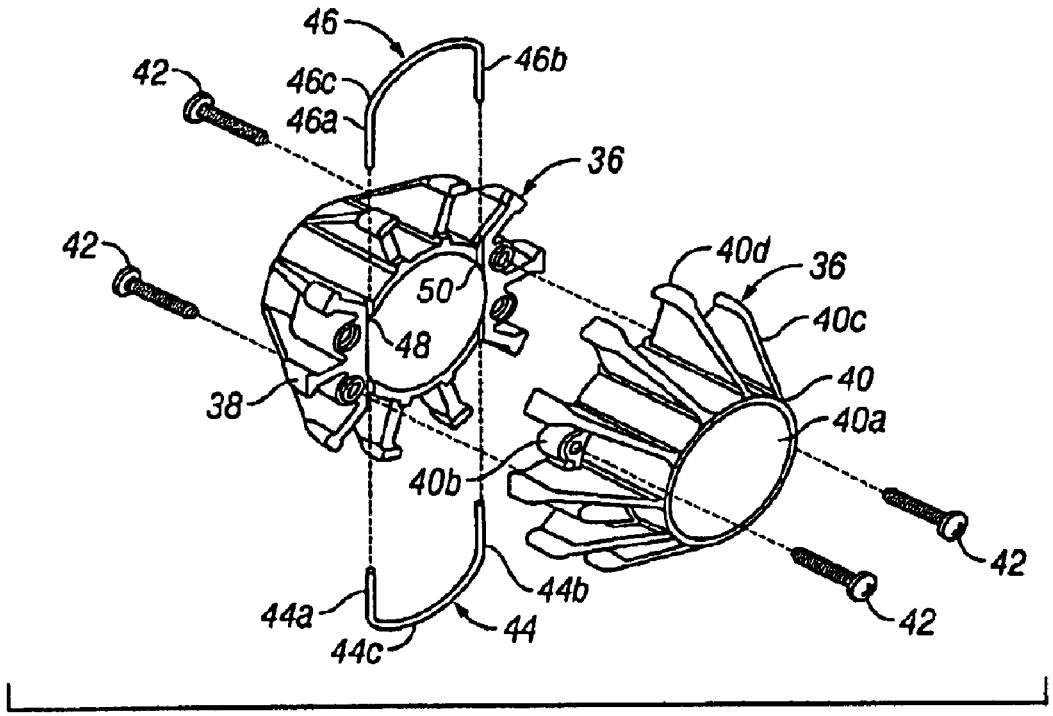
FIG. 3 is an enlarged exploded perspective view of the first embodiment.
Figure 4:
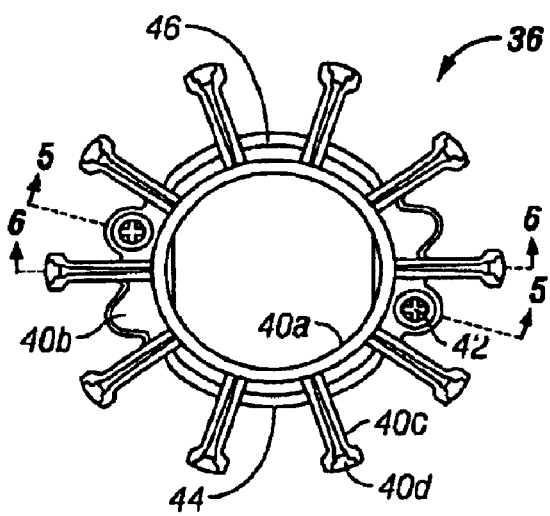
FIG. 4 is an enlarged end elevation view of the guide member of the first embodiment.

Referring to FIG. 2, a first embodiment of our guide 30 is shown clamped to the tubular coil spring 32 of a video pipe inspection system rearward of its rugged camera head 34. Referring to FIGS. 3 and 4, the first embodiment 30 includes a guide member 36 comprised of two molded plastic halves 38 and 40. Each half of the guide member 36, such as 40, has a similar construction including central cylindrical section 40a, screw mounts 40b and radially extending fins 40c. The halves 38 and 40 are held together by four screws 42. The fins 40c terminate in skid pads 40d. Bristles or some other form of appendages could be used in place of the fins 40c to engage the interior wall of the pipe and center the camera head 34 within the pipe.

The inner diameter of the central cylindrical section 40a (FIG. 3) is slightly larger than the outer diameter of the camera head 34 and the outer diameter of the tubular coil spring 32. This allows the two halves 38 and 40 of the assembled guide member 36 to be slid over the camera head 34 to the desired position along the tubular coil spring 32 and removably retained in position by inwardly pushing on a pair of opposing U-shaped pins 44 and 46 (FIG. 3). Each of the U-shaped pins such as 46 has a pair of parallel straight leg segments 46a and 46b that are joined by an arcuate shaped intermediate segment 46c. The straight leg segments such as 46a and 46b of each of the pins, such as 46, are engaged with the tubular coil spring 32 on opposite sides thereof by sliding the straight leg segments 46a and 46b with respect to the guide member 36 along respective insertion axes that are substantially perpendicular to the longitudinal central axis of the tubular coil spring 32.

Figure 5:
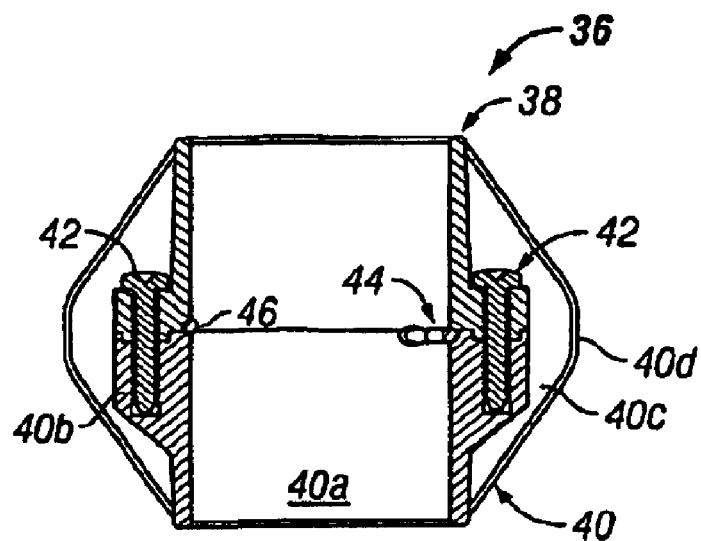
FIG. 5 is a longitudinal sectional view of the guide member of the first embodiment taken along line 5—5 of FIG. 4.
Figure 6:
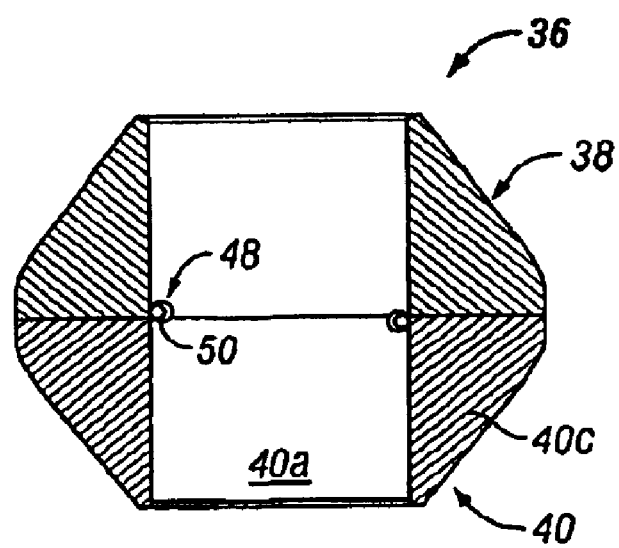
FIG. 6 is a longitudinal sectional view of the guide member of the first embodiment taken along line 6—6 of FIG. 4.

The guide member 36 is formed with receptacles for receiving the straight leg segments, such as 46a and 46b, of each of U-shaped pins 44 and 46. The receptacles in the first embodiment 30 are formed as complementary grooves 48 and 50 (FIGS. 3 and 6) molded into the mating faces of the halves 38 and 40. As best seen in FIG. 5, the receptacles formed by the grooves 48 and 50 are longitudinally spaced to ensure that the straight leg segments such as 46a and 46b of each of the U-shaped pins such as 46 will be inserted between the same two adjacent coils of the tubular coil spring 32. This is accomplished by making one of the grooves 48 deeper than its mating groove 50. Effectively the straight leg segments 44a and 46a are longitudinally offset from the straight leg segments 44b and 46b by half the thickness of the wire that forms the tubular coil spring 32, and therefore the pins 44 and 46 are angled to match the pitch of the helical coils of the spring 32. Thus the guide member 36 is formed with receptacles formed by the grooves 48 and 50 for receiving the straight leg segments, 44a, 44b, 46a and 46b, of the pair of U-shaped pins 44 and 46, the receptacles being longitudinally spaced to ensure that the straight leg segments of each of the U-shaped pins will be inserted between the same two adjacent coils of the tubular coil spring 32.

When both of the pins 44 and 46 are fully inserted as illustrated in FIG. 4, the opposing ends of their straight segments such as 44b and 46b abut each other or nearly abut each other. Each curved intermediate segment, such as 46c, is positioned just above the central cylindrical sections, such as 40a, of each of the halves 38 and 40. The pins 44 and 46 are preferably made of spring steel. Because the straight segments, such as 46a and 46b of the pin 46, extend between adjacent coils of the tubular coil spring 32, the first embodiment 30 can be spun or rotated relative to the central axis of the spring 32 to thread the first embodiment 30 to the desired longitudinal position. The pins 44 and 46 can be pulled outwardly until their curved intermediate segments, such as 46c, abut the undersides of the adjacent skid pads, such as 40d. This withdraws the straight leg segments, such as 46a and 46b, from between the adjacent coils of the spring 32. This allows the first embodiment 30 to be slid forwardly over the spring 32 and over the camera head 34 to completely remove the first embodiment 30 from the video pipe inspection system. One vertical side surface of a fin, such as 40d, that faces a corresponding pin 44 or 46 is formed with a detent (not visible) into which the corresponding curved intermediate segment such as 46c can snap into place. This provides a means for removably holding the pin in its fully inserted position.

Figure 7:
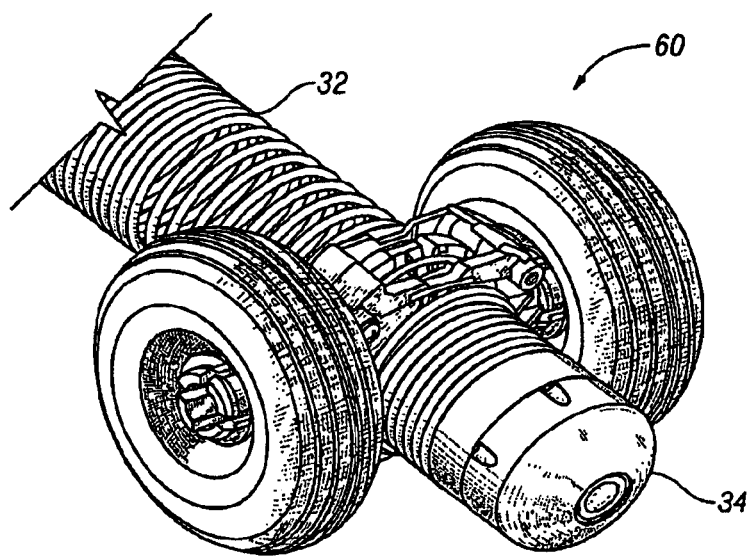
FIG. 7 is a perspective view illustrating a second embodiment of the present invention.
Figure 8:
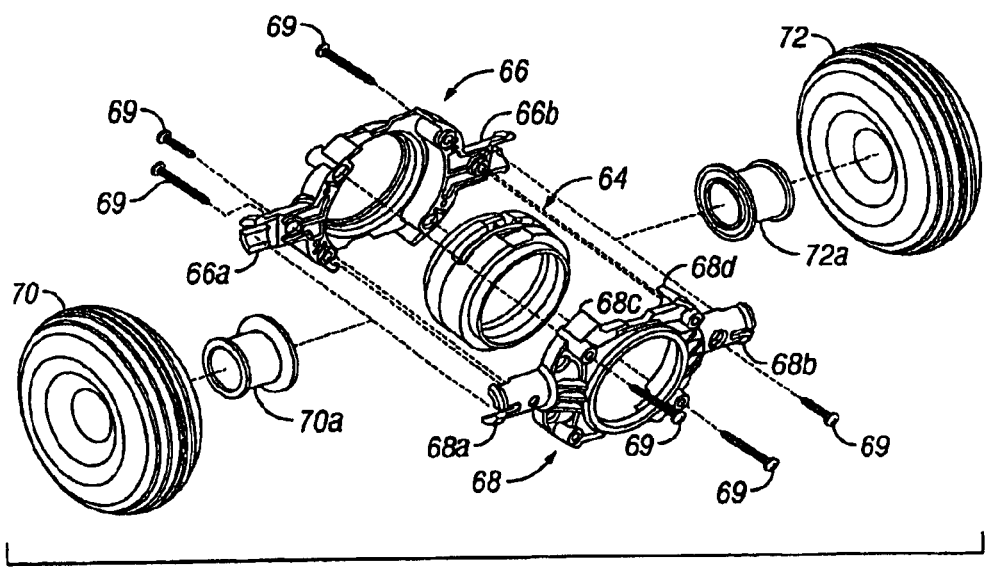
FIG. 8 is an enlarged exploded perspective view of the second embodiment.

FIG. 7 is a perspective view illustrating a second embodiment 60 of the present invention in the form of a dolly that is mounted around the tubular coil spring 32 aft of the camera head 34. The second embodiment 60 comprises a guide member in the form of an inner capture ring assembly 64 (FIG. 8). An outer yoke assembly is made of molded plastic clam shell halves 66 and 68 held together by screws 69. The yoke assembly surrounds the capture ring assembly 64 and is freely rotatable about the same. The halves 66 and 68 of the outer yoke assembly have mating sections 66a and 68a and 66b and 68b that form a pair of opposed co-linear axles that rotatably support wheels 70 and 72 that engage the interior wall of the pipe. The wheels 70 and 72 have internal sleeves or bushings 70a and 72a. The mating sections 66a, 66b, 68a and 68b that form the axles are splined and have retaining lips on their outer ends, allowing the bushings 70a and 72a to snap fit over the axles and be retained on the same. The wheels 70 and 72 are preferably made of soft synthetic rubber of other suitable elastomeric material. Exemplary wheels for this purpose are commercially available in the United States of America under the DU-BRO® brand and are of the type frequently used on the landing gear of radio controlled model airplanes. The size of the wheels 70 and 72 depends upon the size of the pipe, but one exemplary size of the aforementioned brand of wheels is three inches (76 millimeters) in external diameter.

Figure 9:
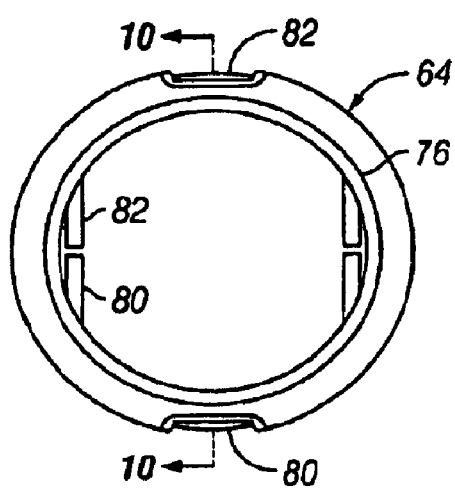
FIG. 9 is an enlarged end elevation view of the inner capture ring of the second embodiment.
Figure 10:
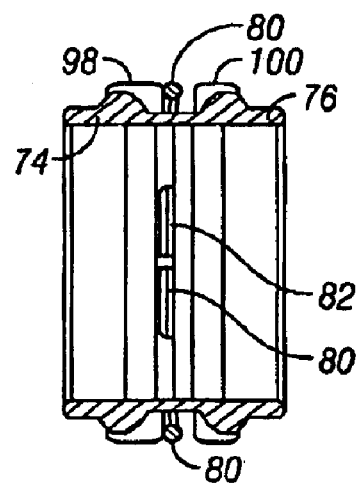
FIG. 10 is a longitudinal sectional view of the inner capture ring taken along line 10—10 of FIG. 9.
Figure 11:
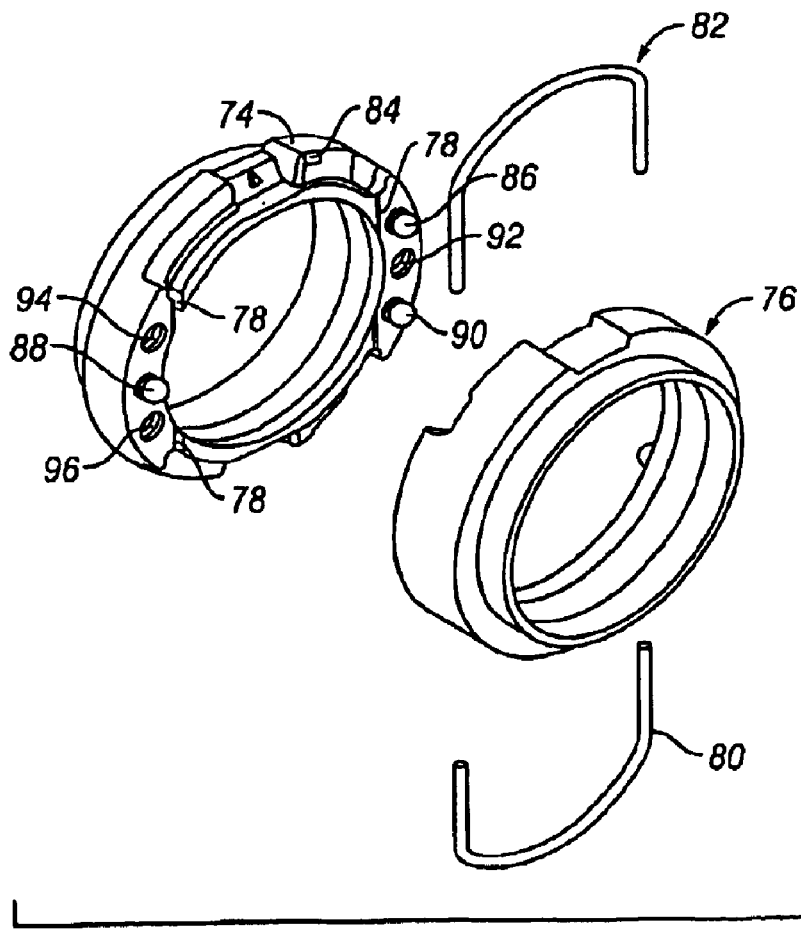
FIG. 11 is an enlarged exploded view of the inner capture ring and pair of U-shaped pins of the second embodiment.

The capture ring assembly 64 comprises two mating halves 74 and 76 (FIG. 11) with receptacles such as 78 formed in the mating surfaces thereof for slidably receiving a pair of opposed U-shaped pins 80 and 82. Again the pin receptacles, such as 78 are formed so that the pins 80 and 82 will be angled with respect to the longitudinal central axis of the tubular coil spring 32 to match its pitch. As with the first embodiment 30, the straight leg segments of the U-shaped pins 80 and 82 of the second embodiment 60 slide between the same two adjacent coils of the tubular coil spring 32. Each of the mating halves such as 74 is formed with a notch 84 beneath which the curved intermediate segment of the corresponding one of the U-shaped pins 80 and 82 can be pushed to removably hold the pin in its fully inserted position. The fully inserted positions of the pins 80 and 82 are illustrated in FIG. 9. Three locator projections 86, 88 and 90 (FIG. 11) on the half 74 mate with three locator holes (not visible) in the other half 76 of the inner capture ring assembly 64. Three locator projections (not visible) on the half 76 mate with three locator holes 92, 94 and 96 in the other half 76 of the inner capture ring assembly 64. Curved retainer caps such as 98 and 100 (FIG. 10) partially surround the exterior circumference of the halves 74 and 76.

When the pins 80 and 82 of the second embodiment are withdrawn, the ends of their curved intermediate segments eventually abut shoulders, such as 68c and 68d (FIG. 8), of the yoke assembly halves 66 and 68. This allows the straight leg segments of the pins 80 and 82 to be fully withdrawn from engagement with the tubular coil spring 32 without falling out of the inner capture ring assembly 64. Once the pins 80 and 82 have been slid to their fully withdrawn positions, the second embodiment 60 can be slid forwardly over the spring 32 and over the camera head 34 to remove the second embodiment from the pipe inspection system.

It may be desirable to mount two of the first embodiments 30 at longitudinally spaced locations along the spring 32. A single second embodiment 60 which forms a dolly can typically be used although the use of two such dollies mounted at longitudinally spaced locations along the spring 32 will ensure that the field of view of the camera head 34 is aligned with the central axis of the pipe. The ability of the wheels 70 and 72 to rotate about the central axis of the pipe facilitates insertion and withdrawal of the camera head 34.

Having described a pair of preferred embodiments of our guide in detail, modifications and adaptations thereof will occur to those skilled in the art. For example, instead of sliding over the camera head 34, the guide member 36 could have a clam shell construction allowing it to be clamped around the tubular coil spring 32. This arrangement would accommodate systems having a camera head 34 with a relatively larger outer diameter than that of the spring 32. In the second embodiment 60 a releasable locking mechanism could be provided for locking the relative rotational position of the inner capture ring assembly 64 relative to the outer yoke assembly made of the halves 66 and 68. Furthermore, it is not necessary to have the rotational axes of the wheels 70 and 72 co-linear. These axes could extend in a gull wing configuration. The second embodiment could also have four axles instead of two axles so that four separate wheels would support the camera head 34. The dolly could utilize only a single wheel. Multiple wheels could be mounted on the same axle. Therefore, the protection afforded our invention should only be limited in accordance with the scope of the following claims.

We claim:

1. A guide for a video pipe inspection system including a camera head and a tubular coil spring located in a rearward position relative to the camera head, the tubular coil spring having a longitudinally extending central axis, comprising:

a guide member configured to surround the tubular spring; and at least one pin that is removably engageable with the guide member and the tubular coil spring to retain the guide member in position with respect to the tubular coil spring.

2. The guide of claim 1 wherein the guide member has a plurality of radially extending fins.

3. The guide of claim 1 wherein the guide member includes a pair of wheels.

4. The guide of claim 1 wherein the pin includes at least one straight leg segment that is engaged with the tubular coil by sliding the pin with respect to the guide member along an insertion axis that is substantially perpendicular to the central axis.

5. The guide of claim 1 wherein the pin has a generally U-shaped configuration that includes a pair of parallel straight leg segments joined by an intermediate segment, the leg segments being engaged with the tubular coil on opposite sides thereof by sliding the leg segments with respect to the guide member along respective insertion axes that are substantially perpendicular to the central axis.

6. The guide of claim 1 wherein the guide member is retained in position around the tubular coil spring by a pair of opposing pins each having a generally U-shaped configuration that includes a pair of parallel straight leg segments joined by an intermediate segment, the leg segments of each pin being engaged with the tubular coil on opposite sides thereof by sliding the leg segments with respect to the guide member along respective insertion axes that are substantially perpendicular to the central axis.

7. The guide of claim 1 wherein the guide member includes means for removably holding the pin in a fully inserted position.

8. The guide of claim 1 wherein the pin is inserted between adjacent coils of the tubular coil spring.

9. The guide of claim 6 wherein the guide member is formed with receptacles for receiving the straight leg segments of the pair of U-shaped pins, the receptacles being longitudinally spaced to ensure that the straight leg segments of each of the U-shaped pins will be inserted between the same two adjacent coils of the tubular coil spring.

10. The guide of claim 1 wherein the guide member includes an inner capture ring assembly that receives the pin and an outer yoke assembly that includes means for rotatably supporting at least one wheel that engages an interior wall of the pipe.

11. A guide for a video pipe inspection system including a camera head and a tubular coil spring located in a rearward position relative to the camera head, the tubular coil spring having a longitudinally extending central axis, comprising:

a guide member configured to surround the tubular spring;

a yoke assembly that surrounds the guide member and includes at least one axle;

at least one wheel rotatably mounted on the one axle; and means for releasably holding the guide member at a preselected longitudinal position along the tubular coil spring.

12. The guide of claim 11 wherein the yoke is freely rotatable about the guide member.

13. The guide of claim 11 wherein the releasable holding means includes at least one pin that is removably engageable with the guide member and the tubular coil spring to retain the guide member in position with respect to the tubular coil spring.

14. The guide of claim 12 wherein the pin includes at least one straight leg segment that is engaged with the tubular coil by sliding the pin with respect to the guide member along an insertion axis that is substantially perpendicular to the central axis.

15. The guide of claim 12 wherein the pin has a generally U-shaped configuration that includes a pair of parallel straight leg segments joined by an intermediate segment, the leg segments being engaged with the tubular coil on opposite sides thereof by sliding the leg segments with respect to the guide member along respective insertion axes that are substantially perpendicular to the central axis.

16. The guide of claim 11 wherein the releasable holding means includes a pair of opposing pins each having a generally U-shaped configuration that includes a pair of parallel straight leg segments joined by an intermediate segment, the leg segments of each pin being engaged with the tubular coil on opposite sides thereof by sliding the leg segments with respect to the guide member along respective insertion axes that are substantially perpendicular to the central axis.

17. The guide of claim 12 wherein the guide member includes means for removably holding the pin in a fully inserted position.

18. The guide of claim 15 wherein the guide member is formed with receptacles for receiving the straight leg segments of the pair of U-shaped pins, the receptacles being longitudinally spaced to ensure that the straight leg segments of each of the U-shaped pins will be inserted between the same two adjacent coils of the tubular coil spring.

19. The guide of claim 11 wherein the yoke assembly has a pair of oppositely extending axles, each rotatably supporting a wheel.

20. A guide for a video pipe inspection system including a camera head and a tubular coil spring located in a rearward position relative to the camera head, the tubular coil spring having a longitudinally extending central axis, comprising:

a guide member configured to surround the tubular spring;

a yoke assembly that surrounds the guide member and is rotatable about the guide member, the yoke assembly including a pair of axles;

a pair of wheels each rotatably mounted on a corresponding one of the axles; and means for releasably holding the guide member at a preselected longitudinal position along the tubular coil spring, including a pair of opposing pins each having a generally U-shaped configuration that includes a pair of parallel straight leg segments joined by an intermediate segment, the leg segments of each pin being engaged with the tubular coil on opposite sides thereof by sliding the leg segments with respect to the guide member along respective insertion axes that are substantially perpendicular to the central axis.

* * * * *